(12) United States Patent
Bruzzi et al.

(10) Patent No.: US 10,743,907 B2
(45) Date of Patent: Aug. 18, 2020

(54) THROMBECTOMY DEVICE

(71) Applicant: NATIONAL UNIVERSITY OF IRELAND, GALWAY, Galway (IE)

(72) Inventors: Mark Bruzzi, Galway (IE); Paul Heneghan, Galway (IE); Saeid Kasiri Ghahi, Galway (IE); Gerard O'Sullivan, Galway (IE)

(73) Assignee: National University of Ireland, Galway, Galway (IE)

( * ) Notice: Subject to any disclaimer, the term of this patent is extended or adjusted under 35 U.S.C. 154(b) by 0 days.

(21) Appl. No.: 15/524,851

(22) PCT Filed: Nov. 6, 2015

(86) PCT No.: PCT/EP2015/075995
§ 371 (c)(1),
(2) Date: May 5, 2017

(87) PCT Pub. No.: WO2016/071524
PCT Pub. Date: May 12, 2016

(65) Prior Publication Data
US 2017/0333076 A1    Nov. 23, 2017

Related U.S. Application Data

(60) Provisional application No. 62/077,012, filed on Nov. 7, 2014.

(30) Foreign Application Priority Data

Nov. 7, 2014 (EP) .................................... 14192263

(51) Int. Cl.
*A61B 17/3207* (2006.01)
*A61B 17/22* (2006.01)
(Continued)

(52) U.S. Cl.
CPC .... *A61B 17/320758* (2013.01); *A61B 17/221* (2013.01); *A61B 17/22004* (2013.01);
(Continued)

(58) Field of Classification Search
CPC .... A61B 17/320758; A61B 17/320725; A61B 17/32075; A61B 2017/22067;
(Continued)

(56) References Cited

U.S. PATENT DOCUMENTS 4,909,789 A    3/1990  Taguchi et al.
4,927,426 A *  5/1990  Dretler ................. A61B 17/221
                                                                 604/540
(Continued)

FOREIGN PATENT DOCUMENTS

EP    0 117 519 A1    9/1984
EP    0200668 A2 *  11/1986   ....... A61B 17/22032
(Continued)

OTHER PUBLICATIONS

US 6,348,062 B1, 02/2002, Hopkins et al. (withdrawn)
(Continued)

*Primary Examiner* — Katrina M Stransky
*Assistant Examiner* — Brigid K Byrd
(74) *Attorney, Agent, or Firm* — Bookoff McAndrews, PLLC

(57)    ABSTRACT

A thrombectomy device for removing thrombus from a body lumen comprises an elongated catheter member (2) having a distal part and a proximal part, a thrombus blocking body (5) disposed on the distal part of the catheter member and radially expansible between a contracted orientation and an expanded, thrombus-blocking, orientation, a thrombus capture body (3) disposed on the distal part of the catheter member in an axially spaced-apart relationship to the thrombus blocking body, and radially expansible between a con-
(Continued)

tracted orientation and an expanded, thrombus-capture, orientation, deployment means actuable to deploy and retract the thrombus capture body and thrombus blocking body; and an elongated control arm operably connected to the thrombus capture body. The thrombus capture body is a cage having an inwardly tapering leading end, the elongated control arm is operably connected to the leading end of the cage, and a thrombus extractor or macerator mechanism is disposed within the cage.

18 Claims, 10 Drawing Sheets

(51) Int. Cl.
  A61B 17/221 (2006.01)
  A61B 17/00 (2006.01)
  A61B 90/00 (2016.01)
(52) U.S. Cl.
  CPC .......... *A61B 17/32075* (2013.01); *A61B 17/320725* (2013.01); *A61B 2017/00685* (2013.01); *A61B 2017/00867* (2013.01); *A61B 2017/2212* (2013.01); *A61B 2017/22067* (2013.01); *A61B 2017/22079* (2013.01); *A61B 2017/22084* (2013.01); *A61B 2017/320766* (2013.01); *A61B 2017/320775* (2013.01); *A61B 2090/034* (2016.02)
(58) Field of Classification Search
  CPC .... A61B 2017/22054; A61B 2090/034; A61B 17/3207–2017/320791; A61B 17/221–2017/2217; A61B 2/01–2002/018; A61B 17/22031; A61F 2/013; A61F 2002/015
  See application file for complete search history.

(56) References Cited

U.S. PATENT DOCUMENTS

| | | | |
|---|---|---|---|
| 5,092,839 A | | 3/1992 | Kipperman |
| 5,156,610 A | | 10/1992 | Reger |
| 5,190,557 A | | 3/1993 | Borodulin et al. |
| 5,370,653 A | | 12/1994 | Cragg |
| 5,573,530 A | | 11/1996 | Fleury et al. |
| 5,720,764 A | | 2/1998 | Naderlinger |
| 5,722,401 A | | 3/1998 | Pietroski et al. |
| 5,772,674 A | | 6/1998 | Nakhjavan |
| 5,795,322 A | | 8/1998 | Boudewijn |
| 5,972,019 A | * | 10/1999 | Engelson ............ A61B 17/221 606/200 |
| 6,001,118 A | * | 12/1999 | Daniel ............ A61B 17/22031 606/159 |
| 6,027,520 A | | 2/2000 | Tsugita et al. |
| 6,066,158 A | | 5/2000 | Engelson et al. |
| 6,129,739 A | | 10/2000 | Khosravi |
| 6,146,396 A | | 11/2000 | Konya et al. |
| 6,179,859 B1 | | 1/2001 | Bates et al. |
| 6,179,861 B1 | | 1/2001 | Khosravi et al. |
| 6,203,561 B1 | | 3/2001 | Ramee et al. |
| 6,206,842 B1 | | 3/2001 | Tu et al. |
| 6,371,970 B1 | | 4/2002 | Khosravi et al. |
| 6,383,205 B1 | | 5/2002 | Samson et al. |
| 6,454,775 B1 | | 9/2002 | Demarais et al. |
| 6,530,939 B1 | | 3/2003 | Hopkins et al. |
| 6,544,279 B1 | | 4/2003 | Hopkins et al. |
| 6,558,405 B1 | * | 5/2003 | McInnes ............ A61F 2/013 606/200 |
| 6,610,077 B1 | | 8/2003 | Hancock et al. |
| 6,616,679 B1 | | 9/2003 | Khosravi et al. |
| 6,620,182 B1 | | 9/2003 | Khosravi et al. |
| 6,652,548 B2 | | 11/2003 | Evans et al. |
| 6,656,203 B2 | | 12/2003 | Roth et al. |
| 6,660,014 B2 | | 12/2003 | Demarais et al. |
| 6,695,858 B1 | | 2/2004 | Dubrul et al. |
| 6,702,830 B1 | | 3/2004 | Demarais et al. |
| 6,945,977 B2 | | 9/2005 | Demarais et al. |
| 7,014,647 B2 | | 3/2006 | Brady et al. |
| 7,037,316 B2 | | 5/2006 | McGuckin, Jr. |
| 7,083,633 B2 | | 8/2006 | Morrill et al. |
| 7,220,269 B1 | | 5/2007 | Ansel et al. |
| 7,507,246 B2 | | 3/2009 | McGuckin et al. |
| 7,621,870 B2 | | 11/2009 | Berrada et al. |
| 7,645,261 B2 | | 1/2010 | Hinchliffe |
| 7,645,290 B2 | | 1/2010 | Lucas |
| 7,655,016 B2 | | 2/2010 | Demarais et al. |
| 7,749,220 B2 | | 7/2010 | Schmaltz |
| 7,909,801 B2 | | 3/2011 | Hinchliffe |
| 7,922,741 B2 | | 4/2011 | Gilson et al. |
| 7,955,344 B2 | | 6/2011 | Finitsis |
| 7,955,345 B2 | | 6/2011 | Kucharczyk et al. |
| 7,993,363 B2 | | 8/2011 | Demond et al. |
| 8,038,674 B2 | | 10/2011 | Schmaltz |
| 8,043,313 B2 | | 10/2011 | Krolik |
| 8,043,326 B2 | | 10/2011 | Hancock et al. |
| 8,057,496 B2 | | 11/2011 | Fischer, Jr. |
| 8,057,497 B1 | | 11/2011 | Raju |
| 8,062,258 B2 | | 11/2011 | Demarais et al. |
| 8,066,757 B2 | | 11/2011 | Ferrera et al. |
| 8,070,791 B2 | | 12/2011 | Ferrera et al. |
| 8,088,140 B2 | | 1/2012 | Ferrera et al. |
| 8,092,486 B2 | | 1/2012 | Berrada et al. |
| 8,197,493 B2 | | 6/2012 | Ferrera et al. |
| 8,221,489 B2 | | 7/2012 | Issenmann et al. |
| 8,252,010 B1 | | 8/2012 | Raju |
| 8,303,538 B2 | | 11/2012 | Bonnette et al. |
| RE43,882 E | | 12/2012 | Hopkins et al. |
| 8,343,167 B2 | | 1/2013 | Henson |
| 8,361,095 B2 | | 1/2013 | Osborne |
| 8,366,737 B2 | | 2/2013 | Hancock et al. |
| 8,403,976 B2 | | 3/2013 | Sachar et al. |
| 8,414,543 B2 | | 4/2013 | McGuckin, Jr. et al. |
| 8,430,837 B2 | | 4/2013 | Jenson et al. |
| 8,435,218 B2 | | 5/2013 | Hinchliffe |
| 8,449,566 B2 | | 5/2013 | Finitsis |
| 8,475,487 B2 | | 7/2013 | Bonnette et al. |
| 8,480,697 B2 | | 7/2013 | Kucharczyk et al. |
| 8,486,105 B2 | | 7/2013 | Demond et al. |
| 8,545,514 B2 | | 10/2013 | Ferrera |
| 8,562,639 B2 | | 10/2013 | Khosravi et al. |
| 8,574,262 B2 | | 11/2013 | Ferrera et al. |
| 8,585,713 B2 | | 11/2013 | Ferrera et al. |
| 8,603,122 B2 | | 12/2013 | Pokorney et al. |
| 8,617,201 B2 | | 12/2013 | Hopkins et al. |
| 8,663,259 B2 | | 3/2014 | Levine et al. |
| 8,668,713 B2 | | 3/2014 | Horan et al. |
| 8,679,142 B2 | | 3/2014 | Slee et al. |
| 8,758,424 B2 | | 6/2014 | Sachar et al. |
| 8,764,779 B2 | | 7/2014 | Levine et al. |
| 8,771,289 B2 | | 7/2014 | Mohiuddin et al. |
| 8,784,442 B2 | | 7/2014 | Jones et al. |
| 8,926,680 B2 | | 1/2015 | Ferrera et al. |
| 8,940,003 B2 | | 1/2015 | Slee et al. |
| 8,945,143 B2 | | 2/2015 | Ferrera et al. |
| 8,945,172 B2 | | 2/2015 | Ferrera et al. |
| 8,956,384 B2 | | 2/2015 | Berrada et al. |
| 9,017,294 B2 | | 4/2015 | McGuckin, Jr. et al. |
| 9,050,127 B2 | | 6/2015 | Bonnette et al. |
| 2001/0016751 A1 | | 8/2001 | Trerotola |
| 2001/0031981 A1 | | 10/2001 | Evans |
| 2002/0010487 A1 | * | 1/2002 | Evans ............ A61B 17/221 606/180 |
| 2002/0026211 A1 | | 2/2002 | Khosravi |
| 2002/0188314 A1 | | 12/2002 | Anderson et al. |
| 2003/0055445 A1 | | 3/2003 | Evans et al. |
| 2003/0176884 A1 | | 9/2003 | Berrada |
| 2003/0220667 A1 | | 11/2003 | Van Der Burg |
| 2004/0039435 A1 | | 2/2004 | Hancock |
| 2004/0098033 A1 | | 5/2004 | Leeflang et al. |
| 2004/0219028 A1 | | 11/2004 | Demarais et al. |

(56) References Cited

U.S. PATENT DOCUMENTS

| | | |
|---|---|---|
| 2005/0085826 A1* | 4/2005 | Nair .................... A61B 17/221 606/113 |
| 2006/0030878 A1 | 2/2006 | Anderson et al. |
| 2006/0229645 A1 | 10/2006 | Bonnette et al. |
| 2007/0156170 A1 | 7/2007 | Hancock |
| 2007/0173883 A1 | 7/2007 | Keegan et al. |
| 2007/0250112 A1 | 10/2007 | Ravikumar |
| 2009/0105722 A1 | 4/2009 | Fulkerson et al. |
| 2009/0105737 A1 | 4/2009 | Fulkerson et al. |
| 2009/0292307 A1 | 11/2009 | Razack |
| 2010/0022951 A1 | 1/2010 | Ferrera et al. |
| 2010/0094320 A1 | 4/2010 | Arat et al. |
| 2010/0174309 A1 | 7/2010 | Fulkerson et al. |
| 2010/0185148 A1 | 7/2010 | Gillespie, III |
| 2010/0185230 A1 | 7/2010 | Horan |
| 2010/0217187 A1 | 8/2010 | Fulkerson et al. |
| 2010/0249815 A1 | 9/2010 | Jantzen et al. |
| 2010/0256600 A1 | 10/2010 | Ferrera |
| 2010/0305678 A1 | 12/2010 | Alaswad |
| 2010/0318097 A1 | 12/2010 | Ferrera et al. |
| 2011/0125181 A1 | 5/2011 | Brady et al. |
| 2011/0160757 A1 | 6/2011 | Ferrera et al. |
| 2011/0160760 A1 | 6/2011 | Ferrera et al. |
| 2011/0190797 A1 | 8/2011 | Fulkerson et al. |
| 2011/0190806 A1 | 8/2011 | Wittens |
| 2011/0238106 A1 | 9/2011 | Ferrera et al. |
| 2011/0264132 A1 | 10/2011 | Strauss et al. |
| 2011/0319917 A1 | 12/2011 | Ferrera et al. |
| 2012/0016406 A1 | 1/2012 | Ferrera et al. |
| 2012/0041460 A1 | 2/2012 | Ferrera et al. |
| 2012/0041475 A1 | 2/2012 | Ferrera et al. |
| 2012/0116440 A1 | 5/2012 | Leynov et al. |
| 2012/0239064 A1* | 9/2012 | Cartier ................ A61B 17/221 606/159 |
| 2012/0271231 A1 | 10/2012 | Agrawal |
| 2012/0316600 A1 | 12/2012 | Ferrera et al. |
| 2012/0330350 A1 | 12/2012 | Jones |
| 2013/0030461 A1* | 1/2013 | Marks .................... A61F 2/013 606/200 |
| 2013/0066346 A1 | 3/2013 | Pigott |
| 2013/0102996 A1 | 4/2013 | Strauss |
| 2013/0289589 A1 | 10/2013 | Krolik et al. |
| 2013/0289608 A1 | 10/2013 | Tanaka et al. |
| 2013/0296916 A1 | 11/2013 | Monstadt |
| 2014/0121672 A1 | 5/2014 | Folk |
| 2014/0121758 A1 | 5/2014 | Ferrera et al. |
| 2014/0128905 A1 | 5/2014 | Molaei |
| 2014/0207177 A1 | 7/2014 | Horan et al. |
| 2014/0214067 A1 | 7/2014 | Sachar et al. |
| 2014/0228869 A1 | 8/2014 | Bonnette et al. |
| 2014/0277015 A1* | 9/2014 | Stinis ................ A61B 17/320725 606/159 |
| 2014/0303658 A1 | 10/2014 | Bonnette et al. |
| 2014/0336691 A1 | 11/2014 | Jones |
| 2014/0343585 A1 | 11/2014 | Ferrera et al. |
| 2014/0343595 A1 | 11/2014 | Monstadt |
| 2014/0343596 A1 | 11/2014 | Slee et al. |
| 2015/0005792 A1 | 1/2015 | Ahn |
| 2015/0018928 A1 | 1/2015 | Sachar et al. |
| 2015/0032138 A1 | 1/2015 | Jenson et al. |
| 2015/0032144 A1 | 1/2015 | Holloway |
| 2015/0112376 A1 | 4/2015 | Molaei et al. |
| 2015/0133973 A1 | 5/2015 | Milner et al. |
| 2015/0150672 A1 | 6/2015 | Ma |
| 2015/0157346 A1 | 6/2015 | Ferrera et al. |
| 2015/0182361 A1 | 7/2015 | Ferrera et al. |
| 2015/0196380 A1 | 7/2015 | Berrada et al. |
| 2015/0209058 A1 | 7/2015 | Ferrera et al. |
| 2015/0216650 A1 | 8/2015 | Shaltis |

FOREIGN PATENT DOCUMENTS

| | | |
|---|---|---|
| EP | 1310219 B1 | 3/2007 |
| WO | WO 91/04763 A1 | 4/1991 |
| WO | WO 97/17892 A1 | 5/1997 |
| WO | WO 98/50103 A1 | 11/1998 |
| WO | WO 01/08743 A1 | 2/2001 |
| WO | WO 01/19444 A1 | 3/2001 |
| WO | WO 01/39673 A1 | 6/2001 |
| WO | WO 01/74255 A1 | 10/2001 |
| WO | WO 01/87168 A1 | 11/2001 |
| WO | WO 01/28618 A3 | 12/2001 |
| WO | WO 02/11626 A3 | 8/2002 |
| WO | WO 02/11627 A3 | 11/2002 |
| WO | WO 03/018085 A2 | 3/2003 |
| WO | WO 02/094111 A3 | 4/2003 |
| WO | WO 02/094130 A3 | 10/2003 |
| WO | WO 03/077799 A3 | 4/2004 |
| WO | WO 05/046736 A2 | 5/2005 |
| WO | WO 05/055878 A2 | 6/2005 |
| WO | WO 05/112770 A1 | 12/2005 |
| WO | WO 06/107641 A2 | 10/2006 |
| WO | WO 06/110186 A2 | 10/2006 |
| WO | WO 07/061418 A2 | 5/2007 |
| WO | WO 08/097993 A2 | 8/2008 |
| WO | WO 09/021071 A2 | 2/2009 |
| WO | WO 09/067629 A2 | 5/2009 |
| WO | WO 09/079539 A1 | 6/2009 |
| WO | WO 09/086154 A2 | 7/2009 |
| WO | WO 09/089297 A2 | 7/2009 |
| WO | WO 09/105710 A1 | 8/2009 |
| WO | WO 09/114046 A2 | 9/2009 |
| WO | WO 09/124288 A1 | 10/2009 |
| WO | WO 09/126935 A2 | 10/2009 |
| WO | WO 09/154441 A1 | 12/2009 |
| WO | WO 10/049121 A2 | 5/2010 |
| WO | WO 10/082187 A1 | 7/2010 |
| WO | WO 10/082188 A1 | 7/2010 |
| WO | WO 11/021119 A1 | 2/2011 |
| WO | WO 11/079111 A1 | 6/2011 |
| WO | WO 12/065748 A1 | 5/2012 |
| WO | WO 12/156069 A1 | 11/2012 |
| WO | WO 13/109756 A2 | 7/2013 |
| WO | WO 14/004244 A1 | 1/2014 |
| WO | WO 14/055609 A1 | 4/2014 |
| WO | WO 14/070405 A1 | 5/2014 |
| WO | WO 14/074318 A1 | 5/2014 |
| WO | WO 14/085590 A1 | 6/2014 |
| WO | WO 14/127389 A2 | 8/2014 |
| WO | WO 14/127738 A1 | 8/2014 |
| WO | WO 14/141226 A1 | 9/2014 |
| WO | WO 14/150013 A1 | 9/2014 |
| WO | WO 14/154137 A1 | 10/2014 |
| WO | WO 15/057796 A1 | 4/2015 |

OTHER PUBLICATIONS

International Search Report and Written Opinion of International Application No. PCT/IE2014/000005, dated Jul. 7, 2014, (15 pages).

International Search Report and Written Opinion in pending International Application No. PCT/EP2015/075995 dated Apr. 21, 2016 (16 pages).

* cited by examiner

THROMBECTOMY DEVICE

CROSS-REFERENCE TO RELATED APPLICATIONS

This application is the U.S. national stage entry under 35 U.S.C. § 371 of International Application No. PCT/EP2015/075995, filed on Nov. 6, 2015, which claims priority to European Patent Application No. 14192263.3, filed on Nov. 7, 2014, and U.S. Provisional Application No. 62/077,012, filed Nov. 7, 2014.

TECHNICAL FIELD

The invention provides a device for removing matter such a thrombus from a body lumen such as a blood vessel. In particular, the invention provides a thrombectomy device for removing thrombus from large or tapered blood veins.

BACKGROUND TO THE INVENTION

Thrombectomy devices employing a thrombus capture body and a thrombus blocking body are known from U.S. Pat. Nos. 6,695,858 and 7,220,269 and comprise an elongated catheter member having a distal part and a proximal part, a thrombus blocking body disposed on the distal part of the catheter member and radially expansible between a contracted orientation and an expanded, thrombus-blocking, orientation, a thrombus capture body disposed on the distal part of the catheter member in an axially spaced-apart relationship to the thrombus blocking body, and radially expansible between a contracted orientation and an expanded, thrombus-capture, orientation having an open leading end for receipt of thrombus, deployment means actuable to deploy and retract the thrombus capture body and thrombus blocking body, and control means operable to provide relative movement between the thrombus capture body and the thrombus blocking body. Specifically, the actuation means of these devices is designed to maintain the thrombus capture body in a stationary position, while moving the thrombus blocking body towards the thrombus capture body. While these devices have shown limited success with removal of short thrombus from blood vessels, they do not adequately remove longer thrombus. This problem is illustrated in Comparative FIGS. 14A and 14B, which shows a blood vessel B containing a long thrombus C, and a device of the prior art located for removal of the thrombus. Actuation of the device causes the blocking member D to move in the direction of arrow E (FIG. 14A), while the thrombus capture body F remains stationary. It can be seen from FIG. 14B that, due to the length of the thrombus C, movement of the thrombus blocking member D does not translate to thrombus being pushed into the capture body F, but rather causes the thrombus C to clog up. US 2011/0202088 describes a similar thrombectomy device to those described above. FIG. 13 of this document describes a device having a distal collapsible collector assembly 412 that in use is pulled towards the proximal collector assembly 416. A problem associated with this device is that the circumferential edge of the collector 412 would catch on any obstacles causing the collector to flare.

US2002/0010487 describes an expansible shearing catheter for thrombus removal. In one embodiment (FIG. 25), the device comprises an expansible occlusion member located distally of the shearing basket that is configured to prevent flow downstream beyond the occlusion member and is located a distance distally of the thrombus. Treatment of the lesion involves pushing the shearing catheter downstream towards and into contact with the thrombus, where the action of the outer basket and inner rotating basket cause the break-up of the thrombus. The use of this embodiment does not involve compression of thrombus between the occlusion body and shearing basket; rather, the occlusion body is located during use a distance from the thrombus and functions to occlude blood flow downstream of the thrombus.

It is an object of the invention to overcome at least one of these problems.

STATEMENTS OF INVENTION

The Applicant has discovered that the device according to US2002/0010487 in which the shearing basket is located proximal of the thrombus and during use is consequently pushed into contact with the thrombus by an elongated control arm, suffers from reduced force being imposed on the thrombus by the thrombus capturing body due to the bending flexibility of the elongated body. Additionally there is the risk of the control arm buckling during use due to the length of the arm and the stresses applied to the arm when it is pushing the shearing basket into contact with the thrombus. Additionally, in applications when the shearing basket is pushed downstream in the vessel, where the vessel progressively tapers outwardly, the effectiveness of the shearing basket decreases due to the increasing diameter of the vessel. The Applicant has overcome the problems with the device of US2002/0010487, and the devices of the other prior art documents mentioned above, by providing a thrombectomy device according to the preamble of Claim 1, and in which the thrombus capture body is located distally of the thrombus blocking body.

An embodiment of the invention is illustrated in FIG. 1. As the thrombus capture body is located distally of the thrombus blocking body, and as the elongated control arm is operably connected to a leading end of the thrombus capture body, this results in the thrombus capture body being pulled by its leading end into contact with the thrombus. This has the effect of reducing the compression forces exerted on the control arm, and reduces the risk of the control arm bucking. In addition, in applications where the catheter is introduced into a vessel in a downstream direction, the use of a thrombectomy device having a capture body located distally of the blocking body has the advantage that during use the movement of the capture body will be upstream, where the vessel progressively narrows, thereby maintaining contact between the capture body and the wall of the vessel.

Accordingly, in a first aspect, there is provided a thrombectomy device for removing matter from a body lumen, the device comprising:
- an elongated catheter member (2) having a distal part and a proximal part;
- a thrombus blocking body (5) disposed on the distal part of the catheter member and radially expansible between a contracted orientation and an expanded, thrombus-blocking, orientation;
- a thrombus capture cage (3) disposed on the distal part of the catheter member in an axially spaced-apart relationship to the thrombus blocking body, and radially expansible between a contracted orientation and an expanded, thrombus-capture, orientation, the thrombus capture cage comprising an inwardly tapering leading end facing the blocking body and having apertures for receipt of matter;

deployment means actuable to deploy and retract the thrombus capture cage and thrombus blocking body;

an elongated control arm operably connected to the thrombus capture cage and configured to move the thrombus capture cage axially along the body lumen, wherein the elongated control arm is operably connected to the leading end of the cage; and a thrombus extractor or macerator mechanism is disposed within the thrombus capture body.

in which the thrombus capture cage is ideally located distally of the thrombus blocking body.

In one embodiment, the device includes a control mechanism adapted to vary the force applied by one or both of the thrombus capture cage or blocking body against the vessel wall.

In one embodiment, the control mechanism comprises a biasing element adapted to bias the thrombus capture cage or blocking body into an expanded orientation. This helps maintain contact between the cage and vessel wall, irrespective of whether the cage is being advanced downstream or upstream in the vessel.

In one embodiment, the thrombus capture cage or blocking body are self-expanding.

In one embodiment, the thrombus blocking body is shaped to dovetail with the leading end of the thrombus capture cage. This arrangement facilitates movement of thrombus into the capture cage, and helps ensure that all thrombus is forced into the cage.

In one embodiment, the blocking body is adapted for deformation or reconfiguration upon application of an external force to a shape suitable for dovetailing with the leading end of the cage.

In one embodiment, the external force is the thrombus capture cage abutting the blocking body.

In one embodiment, the blocking body includes an axial extension configured to effect deformation or reconfiguration of the blocking body while the capture cage and blocking body are spaced-apart.

In another aspect, the invention provides a thrombectomy device for removing matter from a body lumen, the device comprising:

an elongated catheter member having a distal part and a proximal part;

a thrombus capture body disposed on the distal part of the catheter member and radially expansible between a contracted orientation and an expanded, thrombus-capture, orientation;

optionally, a thrombus blocking body disposed on the distal part of the catheter member and radially expansible between a contracted orientation and an expanded, thrombus-blocking, orientation;

deployment means actuable to deploy and retract the thrombus capture body and thrombus blocking body; and an elongated control arm operably connected to the thrombus capture body and configured to move the thrombus capture body axially along the body lumen, characterised in that the device comprises vibration means including vibration actuation means configured to vibrate at least one of the thrombus capture body, thrombus blocking body, or the catheter body.

Preferably, the device comprises rotation means operable to rotate the thrombus capture body about an axis of the catheter member. The Applicant has found that both axial and rotational movement of the capture member achieves better removal of thrombus from the lumen of the vessel.

Preferably, the actuation means is operable to rotate the capture member independently of the blocking member.

The cage may be disposed on the distal part of the catheter member either proximally or distally of the thrombus blocking body. Suitably, the cage is located distally of the thrombus capture member.

Typically, the cage comprises an open leading end for receipt of thrombus. The open leading end may comprise a braid or mesh with a mesh size dimensioned to allow thrombus pass into the cage. Preferably, the cage has a substantially closed trailing end, which can be for example a braid or mesh having a mesh size dimensioned for capture of thrombus. In a preferred embodiment, the cage comprises an open leading end comprising a braid or mesh with a mesh size dimensioned to allow thrombus pass into the cage and a substantially closed trailing end comprising a braid or mesh having a mesh size dimensioned for capture of thrombus. The terms "leading end" means the end of the cage facing the blocking member, and the "trailing end" means the end of the cage opposite the leading end.

The thrombus macerator typically comprises a device configured to rotate, for example one or more rotating elements such as wires or brushes configured to come into contact with thrombus located within the cage and dislodge the thrombus and/or break-up the thrombus into smaller particles.

The thrombus extractor may be an extractor tube having an open end disposed within the capture body and adapted to remove thrombus that has gathered within the cage. In one embodiment, the device comprises suction means configured to extract thrombus from the cage through the extractor tube. In another embodiment, the extractor may be a helical screw that extends longitudinally along the catheter member and is configured to deliver thrombus from within the capture body to a proximal end of the device. In another embodiment, the device comprises suction means and a helical screw.

Ideally, the cage comprises a thrombus macerator and a thrombus extractor disposed within the cage. Preferably, the macerator is disposed closer to the trailing end of the cage than the extractor.

Preferably, the cage comprises a circumferential edge configured to scrape thrombus from the body lumen. Typically, the circumferential edge extends radially around the cage. Typically, the circumferential edge extends around the cage at its widest point. Examples of cages having a circumferential edge are described in PCT/IE2013/000005.

Suitably, the blocking body comprises a cage. Ideally, the blocking body comprises a cage having a leading end configured to prevent ingress of thrombus into the cage. The leading may comprise a fine mesh. In another embodiment, the blocking body is an inflatable balloon. In one embodiment, the blocking body is dimensioned to "dove-tail" or overlap in an axial and radial direction with such leading end of the cage. The blocking body may be deformed or reconfigured to allow such overlapping or dove-tailing dimensions before, during or after the engagement of the capturing body and the blocking body. This may be achieved through suitable compliance of the blocking body and or inverting of the blocking body or other means of adjusting the blocking body so that it is capable of achieving an overlap or dove-tail with the capturing body. Embodiments of the blocking body may include radial expansible inflatable bodies or foam, polymer or metallic structures that have sufficient compliance to overlap the capturing body radially and axially during engagement. These embodiments ensures that thrombus located between the cage and the blocking body is forced into the cage by movement of the cage and blocking body together into a dovetail arrangement.

Preferably, the cage is self-expanding. This means that the cage is biased into an expanded configuration and biased to bear against the wall of the lumen. Thus, the cage applies a force (rather than a displacement) against the wall of the lumen and can reduce in size when it encounters an obstruction. The device may include a control mechanism configured to apply a controlled radial force against the wall of the lumen. This may be achieved through the use of shape memory materials such as NiTi alloys and/or through the use of other metal, polymers including but not limited to CoCr, Steel, Ti alloys for construction of the capturing body and or the blocking body. Where this encounters an obstruction, the capture cage navigates through the obstruction.

Typically, the device comprises vibration means including vibration actuation means configured to vibrate at least one of the thrombus capture body, thrombus blocking body, or the catheter body.

Preferably, the vibration means comprises:
 a vibrational rotating member adapted to rotate about a longtitudinal axis of the catheter,
 in which the vibrational rotating member has a centre of gravity that is eccentric to the longtitudinal axis of the catheter; and/or
 a vibrational rotating member adapted to rotate about an axis that is offset with respect of to the longtitudinal axis of the catheter (optionally with or without uneven circumferential friction).

Suitably, the device includes a macerator comprising a rotating macerator member, wherein the vibrational rotating member is operatively connected to the rotating macerator member for rotation therewith.

Typically, the vibrational rotating member is adapted to rotate about an axis that is offset with respect to the longitudinal axis by means of providing sufficient clearance (FIG. 4) within the tube that it rotates. Preferably the vibrational rotating member rotates at an angular velocity that is at or close to the catheter's natural frequency such that it resonates. Additionally, a portion of the catheter including the capture body and the blocking body may be induced to resonate.

Alternatively, the vibrational rotating member may be adapted to have a mass imbalance about the central rotation axis, causing vibration (FIG. 7). Another alternative is to have a cam feature forcing displacement from the central rotation axis. This may occur at high frequency, causing vibration (both FIGS. 5 and 6 could be considered cam features) or at lower frequencies where displacement is more controlled. The device may also comprise a combination of these features that cause vibration, displacement.

The device comprises deployment means actuable to deploy and retract the capture body and the blocking body. Typically, the control means is configured to deploy and retract the capture and blocking bodies independently of each other. In another embodiment, the control means is configured to deploy and retract the capture and blocking bodies together. Various mechanisms for deploying and retracting capture and blocking bodies in catheters are known to the skilled person. For example, when one of the bodies is a cage, two control arms can be employed, a first arm that is connected to a distal end of the cage and a second arm that is connected to a proximal end of the cage, wherein movement of one of the arms relative to the other causes deployment or retraction of the cage. This arrangement is described in PCT/IE2014/000005. In another embodiment, in which one of the bodies is a balloon, a control fluid pumped through a lumen in the catheter can be employed to deploy and retract the balloon. The control fluid may be a liquid or a gas. In another embodiment, the cage, blocking body or both are self-expanding, and in which the deployment means comprises a restraining sheath adapted to cover at least a part of the catheter member and retain the cage, blocking body, or both, in a retracted orientation, whereby removal of the sheath allows the cage, blocking body, or both, expend.

In one embodiment, the capture body, the cage, or both are self-expanding.

In one embodiment, control means adapted to vary the force applied by one or both of the capture or blocking body against the vessel wall is provided. Typically, the control means comprises biasing means (for example a spring means, a constant force spring, a deformable resilient member, or through pneumatic or hydraulic actuation) for biasing each body into an expanded orientation.

The device also includes means for delivering a fluid along the catheter member and releasing the fluid into the cage or between the cage and blocking member or in the blocking member. Thus, the catheter member may comprise a lumen that extends substantially along the length of the catheter member and having a proximal end configured to receive fluid and a distal end configured to release fluid within the cage or between the cage and the blocking member. In one embodiment, the lumen is formed between control arms for the cage. In another embodiment, the device comprises an external sheath in which the catheter member is at least partially disposed within the sheath, wherein the fluid delivery lumen is disposed between the sheath and catheter member.

The invention also provides a method of removing thrombus from a body lumen, which method employs a device according to the invention, the method comprising the steps of: inserting the device having both capture and blocking body in a collapsed orientation into the body lumen containing a thrombus, adjusting the axial or radial position of the device along the body lumen such that one of the capture body and blocking body is located distally of the thrombus and the other of the capture body and blocking body is located proximally of the thrombus, expanding the capture body and blocking body, and moving the thrombus capture body axially towards the thrombus blocking member, whereby thrombus is forced into the thrombus capture member through the open leading end.

In a preferred embodiment, the method includes a step of actuating the macerator or extractor during movement of the capture body towards the blocking body.

In a preferred embodiment, the method includes a step of actuating the macerator and extractor during movement of the capture body towards the blocking body.

In a preferred embodiment, the device comprises vibration means, wherein the method includes a step of actuating the vibration means during movement of the capture body towards the blocking body.

The invention provides a device and method suitable for removing matter such a thrombus, especially long thrombus, from a body lumen such as a blood vessel, especially large or tapered blood vessels. The device find particular application in removing thrombus from large or tapered blood veins.

DEFINITIONS

"Thrombus" should be understood to mean a solid or semi-solid or viscous fluid mass, typically attached to a wall of a blood vessel or lumen. "Long thrombus" should be understood to mean a thrombus having an axial length of at least two or three times the vessel diameter.

"Body lumen" primarily means a blood vessel such as a vein or artery but may include other lumen associated with the lymph, respiratory, urology or GI system. Preferably, the body lumen is as large or tapered vein, examples of which include the femoral, iliac and popliteal veins or vena cava, pulmonary veins.

"Thrombus capture body" means a hollow body capable of being expanded or contacted and having a leading end (the end facing the blocking body) that has apertures dimensioned for receipt of thrombus into the body and a trailing end (the end opposite the leading end) that is closed or has apertures dimensioned for receipt of thrombus. The leading end is inwardly tapering and is connected to the control arm at or close to its apex, such that movement of the control arm pushes or pulls (depending on whether the capture body is located distally or proximally of the blocking body) the capture body axially along the body lumen. The capture body may be a cage. The cage may comprise a mesh or braid structure, having a mesh or braid at the leading end configured for receipt of thrombus, and a finer mesh at the trailing end. The apertures/mesh/braid at the trailing end may be configured to allow small particles of thrombus pass out of the cage and retain larger particles of thrombus. The capture body may be formed by a plurality of longtitudinal structural elements (FIG. 12), or one or more radial winding elements, or a combination of the two.

"Radially expansible" as applied to the cage or blocking body means that the body is expansible between a contracted orientation and an expanded orientation. Generally the bodies are contracted (collapsed) when they are being inserted and removed from a body lumen, and expanded when the are positioned on either side of a thrombus.

"Move the thrombus capture body axially towards the thrombus blocking member" means that the capture body is moved relative to the body lumen towards the blocking body.

The terms "leading end" and "trailing end" should be understood in the context of the intended direction of axial movement of the cage towards the blocking member. The leading end faces the blocking member, and the trailing end is the opposite end of the cage to the leading end.

"Thrombus macerator" should be understood to mean means operable to break thrombus into smaller particles. Various macerators are envisaged for example macerators having rotating elements that are intended to come into contact with thrombus located within the capture body, for example rotating brushes or blades.

"Thrombus extractor" should be understood to mean a means operable to remove thrombus from the capture body. This may include an extractor tube having an open end disposed within the cage, and optionally suction means configured to apply a negative pressure to the open end of the tube. Other extractors include augers or helical screws.

"Dovetail with the leading end of the thrombus capture cage" means that an end of the blocking body facing the capture cage overlaps with the leading end of the cage in an axial and radial direction. This is shown in FIGS. 12 and 13. In FIG. 12, the blocking body when deployed has a shape configured to dovetail with the cage. In FIG. 13, the blocking body has a leading portion that abuts the cage and forces the body to deform into a shape adapted for dovetailing with the cage. In a preferred embodiment, the end of the blocking body inverts (as shown in FIG. 13B). Generally, the shape configured to dovetail with the leading end of the cage is funnel shape.

"Circumferential edge" means an edge that is disposed at least partly circumferentially around the capture body and is configured to cut or shear thrombus from the wall of the body lumen. The edge may be a blade or a wire or a series thereof, for example. The edge is located adjacent to an open end of the capture body such that thrombus dislodged from the wall of the lumen will pass into the open leading end of the capture body.

"Vibration means" should be understood to mean means operable to cause period or random oscillation in the capture body, blocking body, or distal end of the longitudinal catheter member.

BRIEF DESCRIPTION OF THE FIGURES

The invention will be more clearly understood from the following description of some embodiments thereof, given by way of example only, in which:

FIG. A (Comparative) is an illustration of a device of the prior art;

Figure 1:
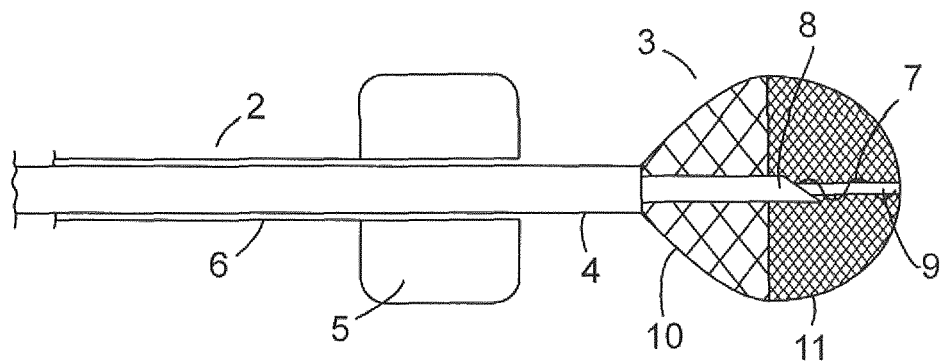
Figure 2:
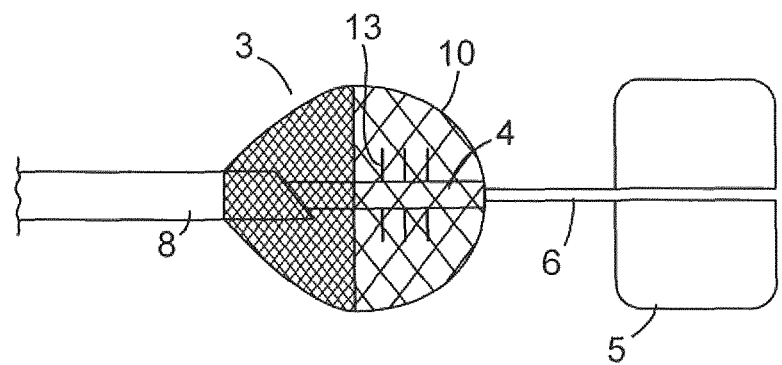
Figure 4:
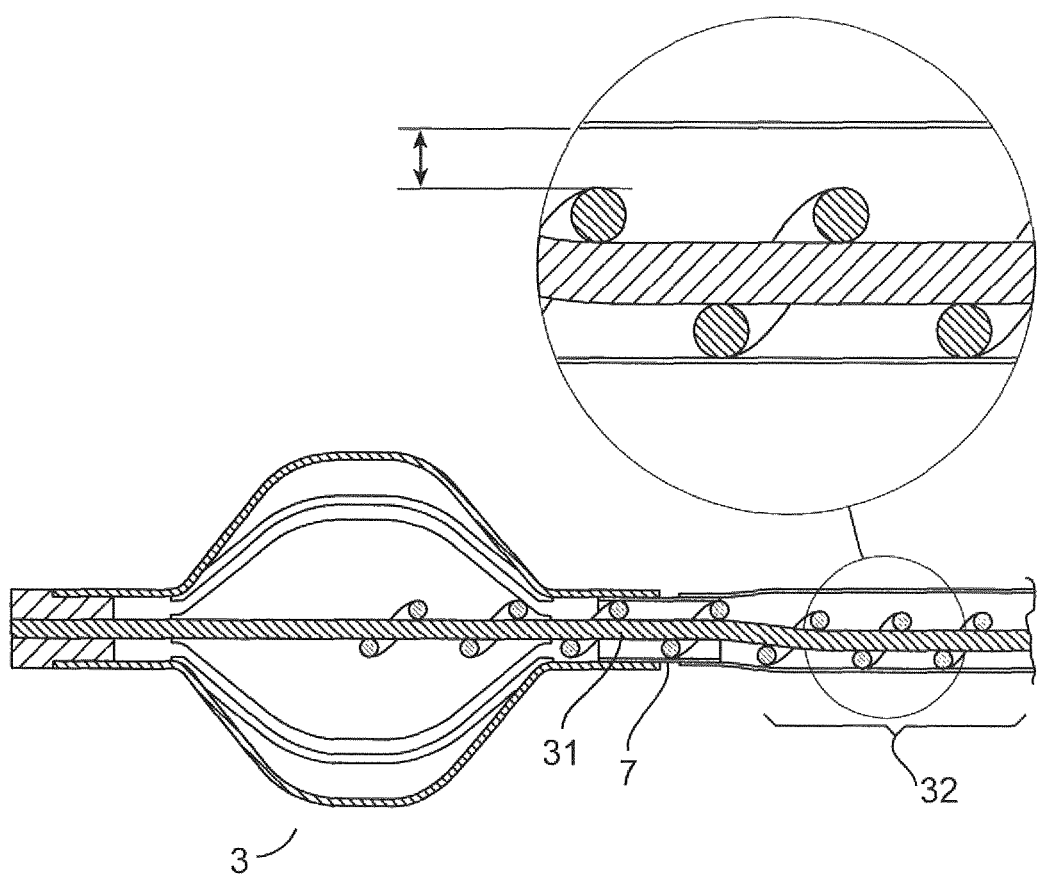
Figure 5:
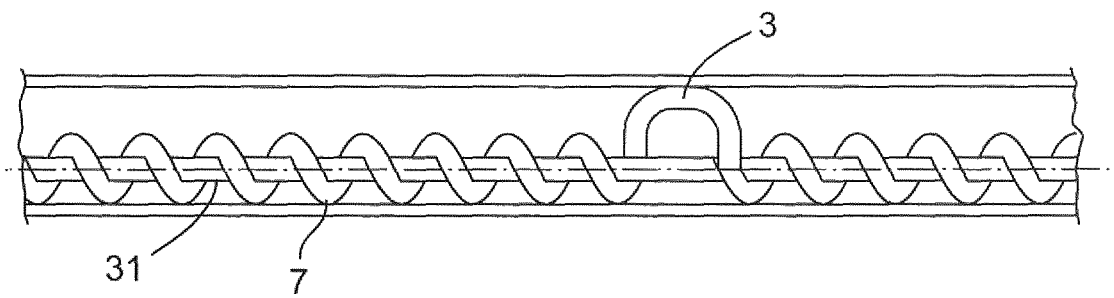
Figure 6:
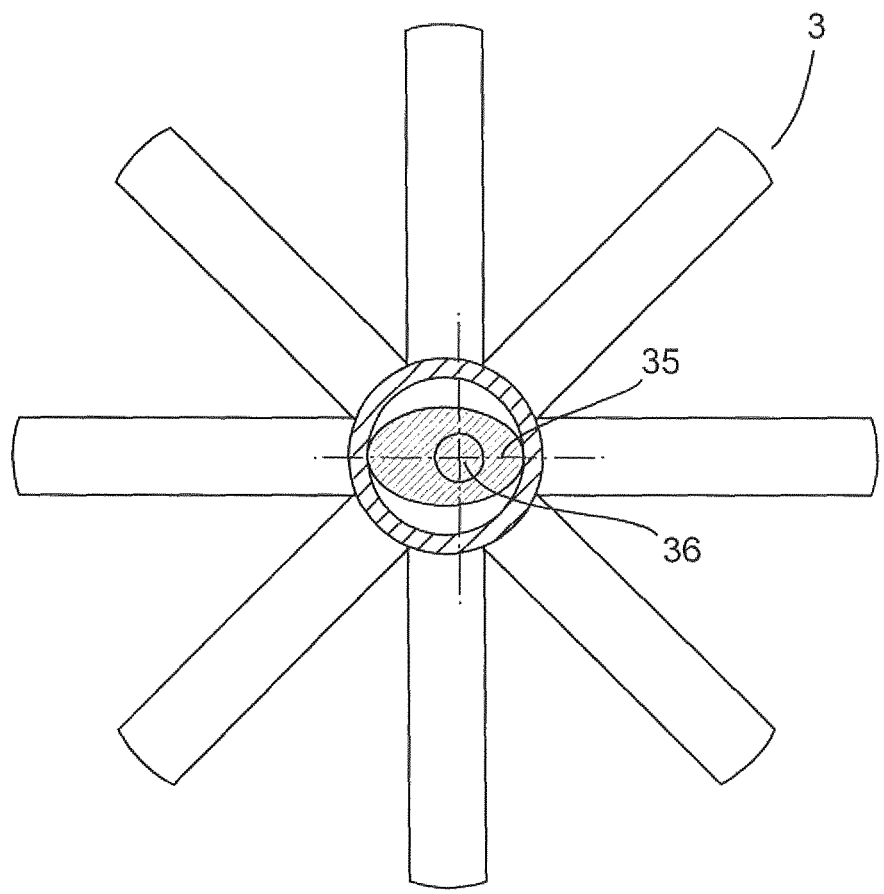

FIG. B (Comparative) is an illustration of a device of Fig. A in a different orientation;

FIG. 1 is a sectional side elevational view of a device according to one embodiment of the invention, having a distal capture body and a proximal blocking body;

FIG. 2 is a sectional side elevational view of a device according to another embodiment of the invention, having a proxial capture body and a distal blocking body;

FIGS. 3A to 3E are illustrations of a method of using the device of the invention to remove a long thrombus from a large blood vessel;

FIG. 4 is an illustration of a device having a vibration mechanism according to the invention comprising a cage and a helical screw extractor mechanism having an axis of rotation that is disposed eccentrically with respect to a longtitudinal axis of the catheter member;

FIG. 5 is an illustration of a device having a vibration mechanism according to an alternative embodiment of the invention comprising an unbalanced helical screw extractor mechanism;

FIG. 6 is an illustration of a device having a vibration mechanism according to an alternative embodiment of the invention comprising a cam mechanism for displacing the cage from the centre of rotation (causing vibration).

Figure 7:
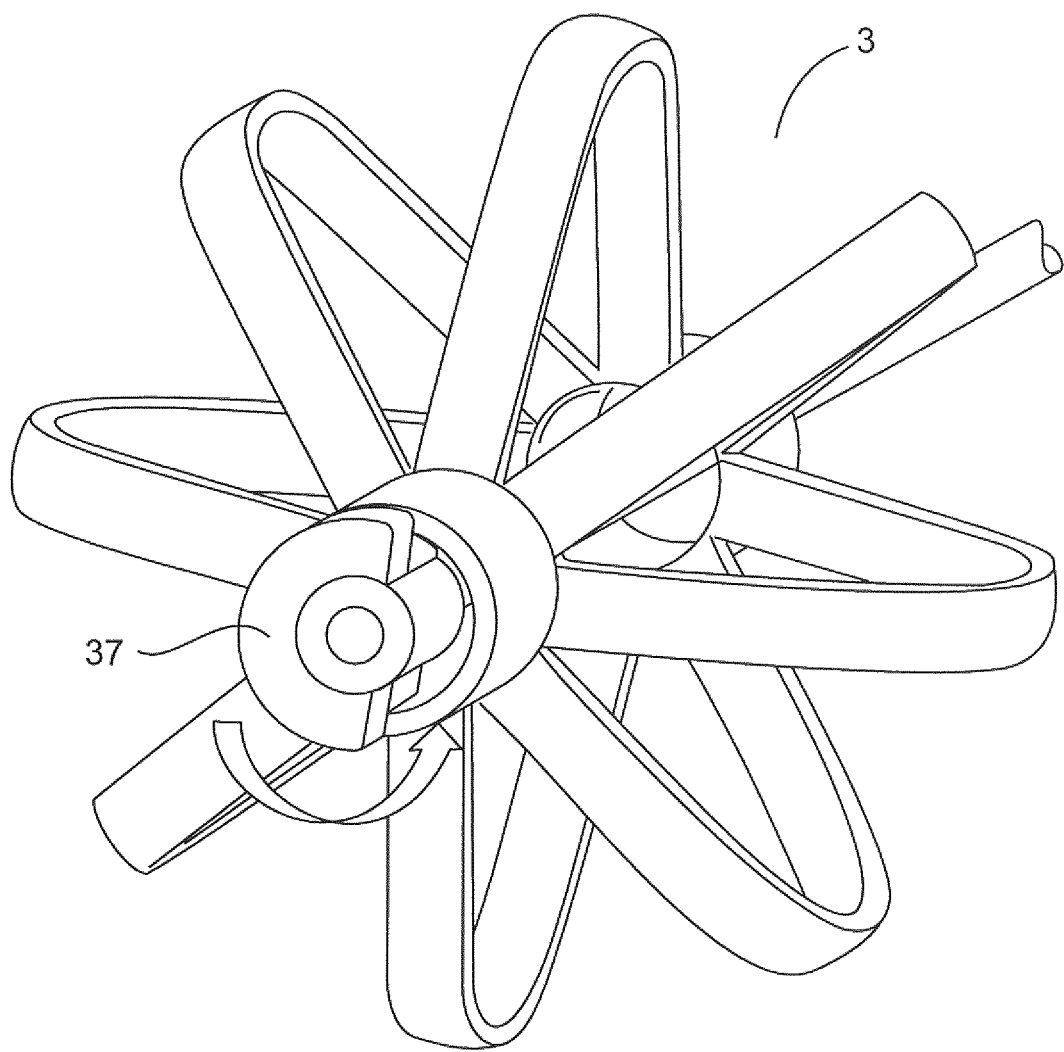
Figure 8:
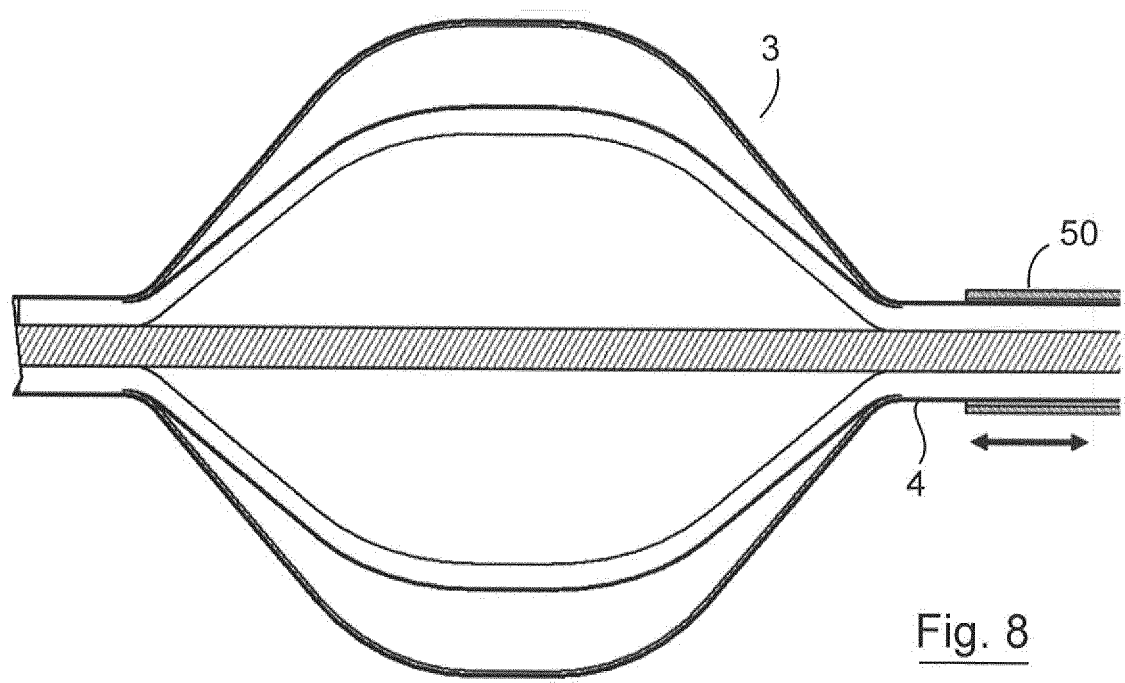

FIG. 7 is an illustration of a device having a vibration mechanism according to an alternative embodiment of the invention comprising an unbalanced weight disposed at an end of the cage and configured to rotate; and FIG. 8. Schematic of the device having a sheath covering the elongated control member and adjustable to cover the cage.

Figure 9:
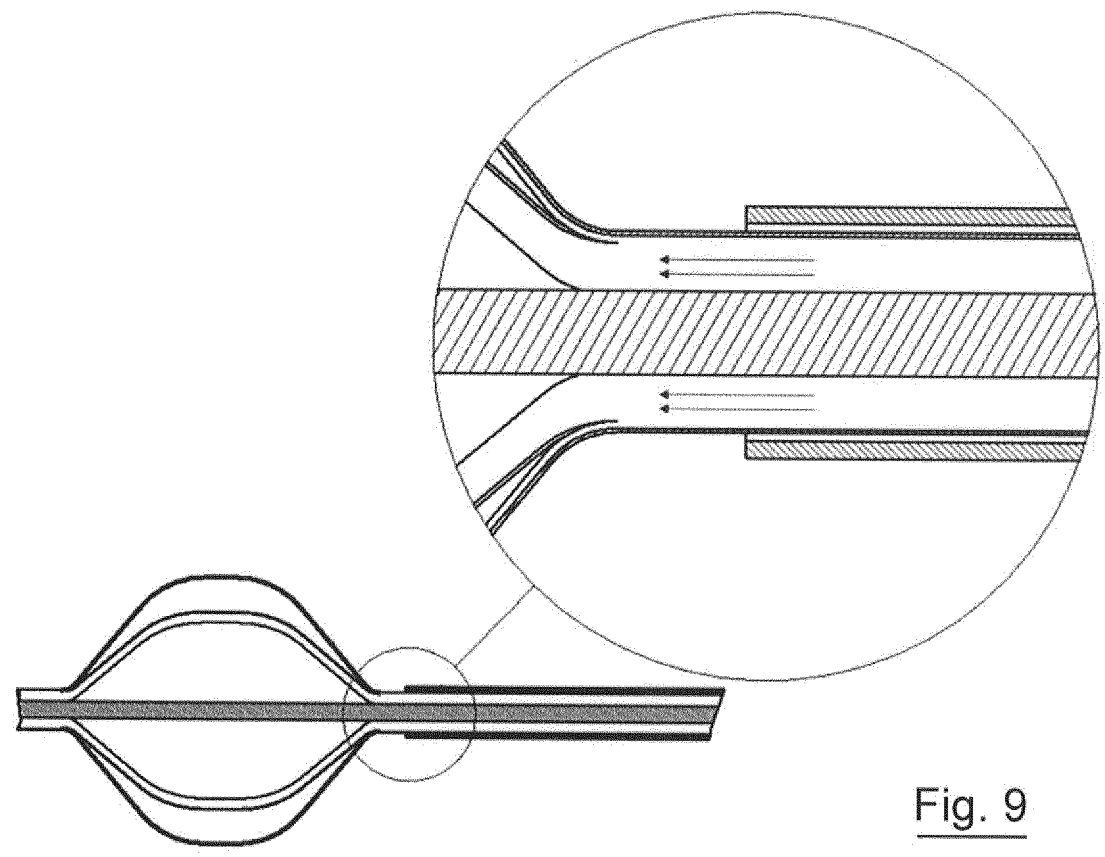

FIG. 9. Schematic of the device of the invention showing how thrombolytic agents may be infused through the extractor.

Figure 10:
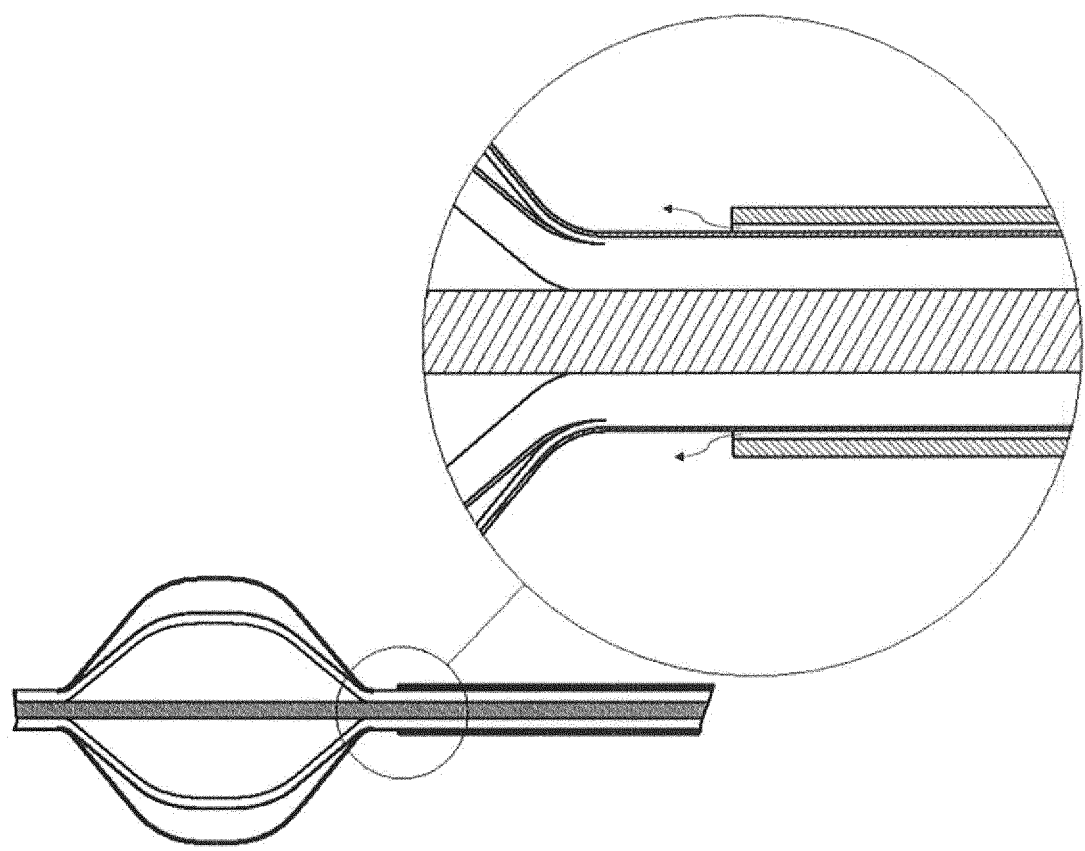

FIG. 10. Schematic of the device of the invention showing how thrombolytic agents may be infused between the extractor and the sheath FIG. 11. Schematic of the device of the invention showing how thrombolytic agents may be infused through holes or perforations formed in the sheath.

Figure 12:
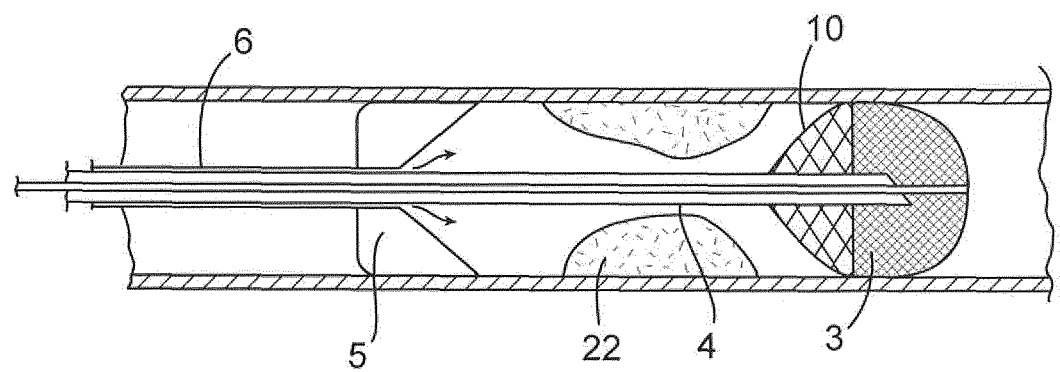

FIG. 12 shows a device similar to FIG. 1 in which the blocking body is shaped to dovetail with the leading end of the cage, and is configured to deliver a thrombolytic liquid to a portion of the body lumen between the cage and blocking body.

Figure 13:
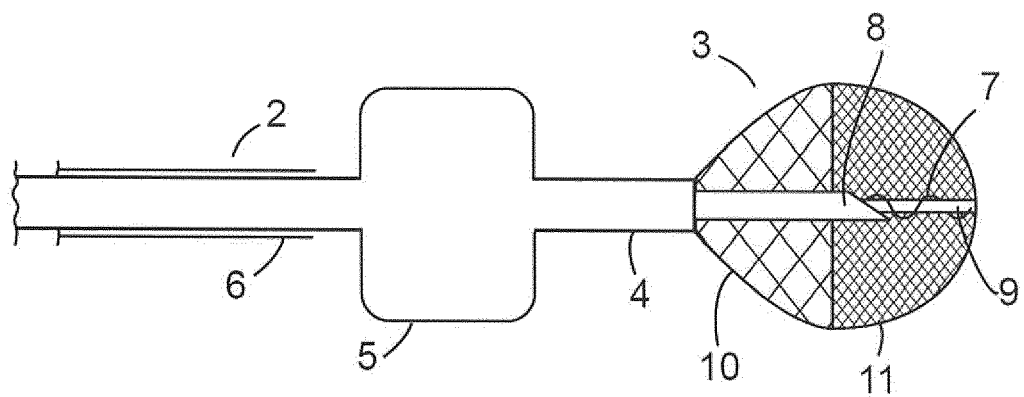
Figure 13:
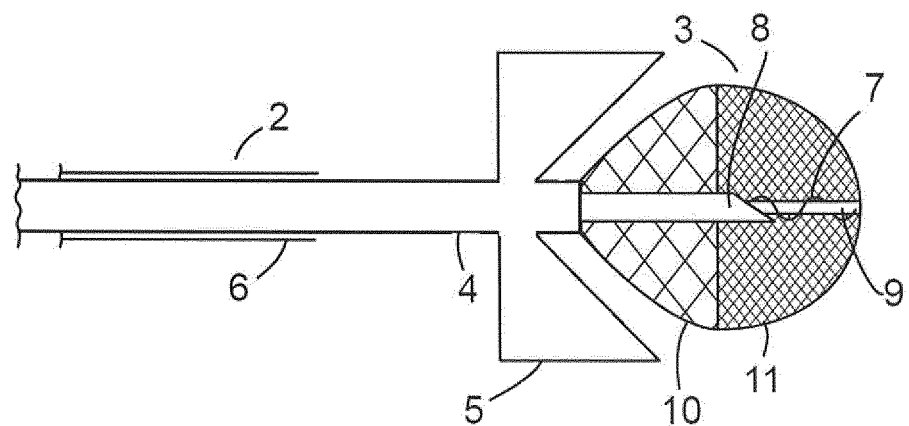

FIG. 13 shows a device similar to FIG. 12 but in which the blocking body is configured to deform (invert) upon engagement with the capture cage into a shape suitable for dovetailing with the capture cage.

Figure 14A:
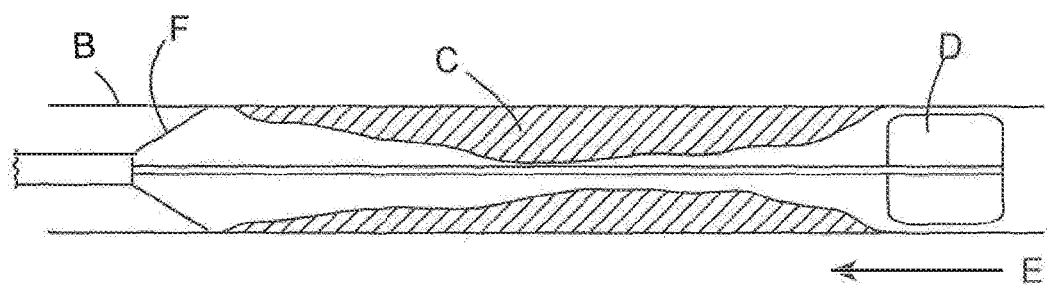
Figure 14B:
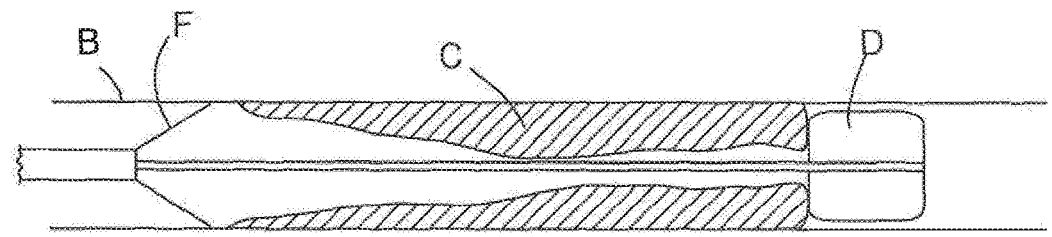

FIG. 14A (Comparative) is an illustration of a device of the prior art;

FIG. 14B (Comparative) is an illustration of a device of FIG. 14A in a different orientation.

DETAILED DESCRIPTION OF THE INVENTION

Referring to FIG. 1, there is illustrated a thrombectomy device according to the invention and comprising an elongated catheter member 2, a proximal blocking body 5 (in this case an inflatable balloon), and a thrombus capture body in the form of a cage 3 having an inwardly tapering trailing end 11 having a fine mesh and the inwardly tapering leading end 10 having a coarse mesh that is adapted for receipt of thrombus into the cage. The device also comprises an extractor tube 8 having an open end disposed distal, proximal or within the cage 3, and an extractor in the form of a helical screw 7 disposed within the extractor tube and having a distal macerator disposed within the cage 3. A control arm 4 is provided for axial movement of the cage 3 and is operably connected to the leading end 10 of the cage 3 to ensure that when the cage is being moved towards the blocking body 5 it is pulled from the leading end 10—this helps prevent the cage flaring when it encounters an obstruction. A second control arm 9 is attached to the trailing end 11 of the cage. Relative movement of the control arms 4 and 9 provides for expansion or contraction of the cage 3. A blocking body control arm 6 may also provided for movement of the blocking body axially along the body lumen.

Referring to FIG. 2, there is illustrated a thrombectomy device according to an alternative embodiment of the invention in which parts identified with reference to the previous embodiment are assigned the same reference numerals. In this embodiment, the cage 3 is located proximally of the blocking body 5, and a macerator in the form of wires 13 is provided on a rotatable control arm 4 forward of the extractor tube 8, whereby rotation of the control arm 4 causes the wires to rotate and macerate thrombus within the cage in the proximity of the wires. In this embodiment, suction means or rotation of a screw (not shown) is provided to extract macerated thrombus from the cage through the extractor tube 12. The control 4 is operably connected to the leading end 10 of the cage 3 for movement of the cage again ensuring that the cage is pushed from its leading end 10.

The use of the devices of the various embodiments of the invention involve common steps, namely insertion of the device into the vessel in which the thrombus is located, in which both capture and blocking body are in a non-deployed, contracted, orientation. Typically, the devices will be advanced along the vessel along a guidewire which is inserted first by the surgeon. The device is advanced along the vessel until the distal body (cage or blocking body, depending on whether the configuration of FIG. 1 or 2 is employed) has passed through and beyond the thrombus, and the proximal body is located within or proximally of the thrombus. Once in this position, the radially expansible capture and blocking body will be deployed on each side of the thrombus or segment of the thrombus, and the cage is advanced towards the blocking body while the blocking body is kept stationary in an axial direction. The macerator or extractor will be actuated during movement of the capture body so that thrombus captured within the cage is macerated within the cage and extracted from the cage along the catheter body and out of the body.

It will be appreciated that the use of a macerator or extractor allows the device remove long thrombus, as the thrombus collected in the cage during use is continually removed from the cage either by the extractor or it is flushed out of the cage by body fluid. This is not achieved with the devices of the prior art. Moreover, the configuration of the device where the cage has a leading end that is attached to the control arm, ensures that the device will not snag or flare when it encounters an obstruction, but can be pulled past the obstruction.

Figure 3:
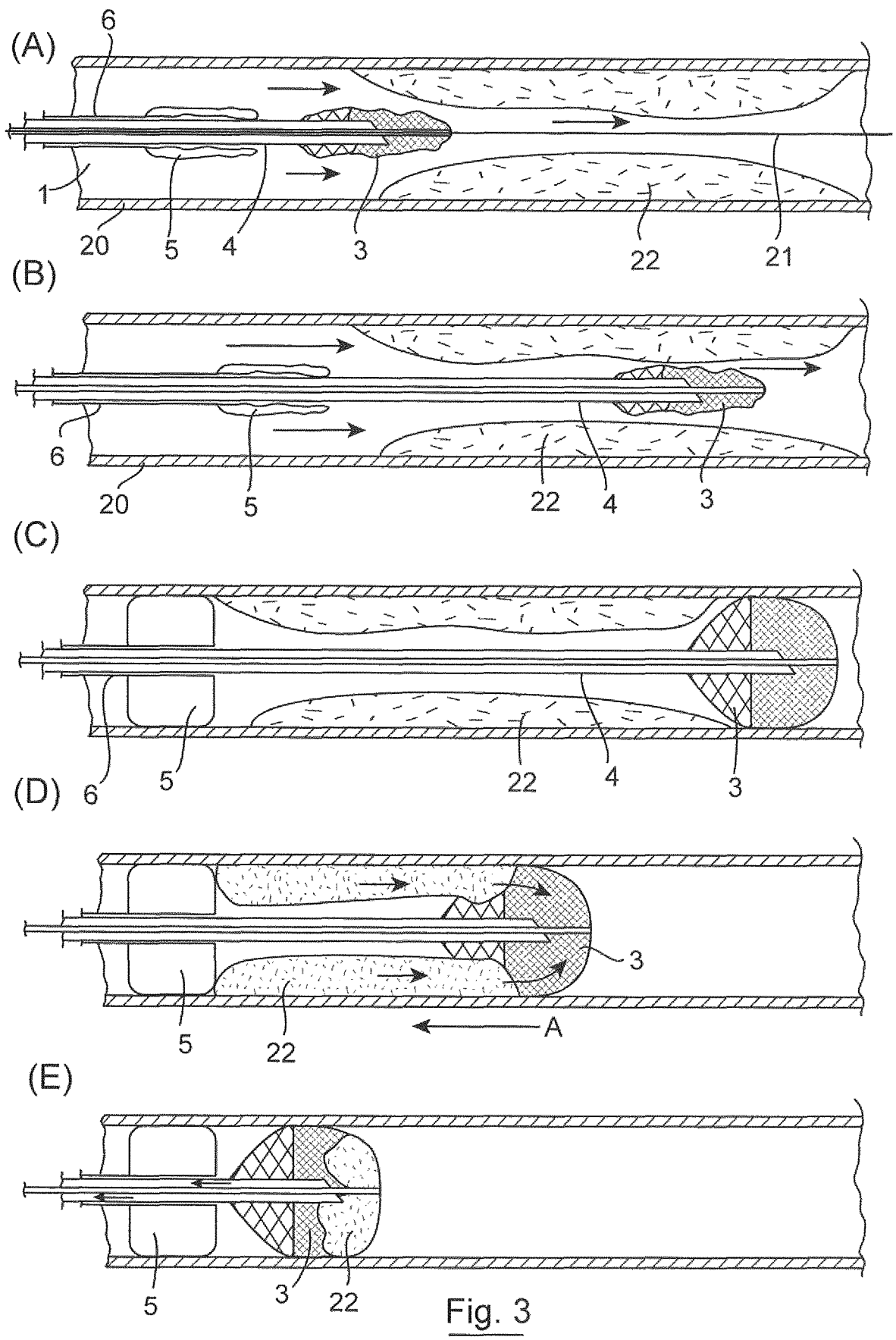

Referring now to FIGS. 3A to 3E, a method of removing thrombus from a blood vessel will be explained in more detail:

FIG. 3A: In the first step, the device of FIG. 1 is advanced through a vessel 20 along a guidewire 21. At this stage, both the blocking body 5 and the cage (capture body) 3 are in a non-deployed configuration.

FIG. 3B: In the second step, the device is advanced along the vessel 20 until the cage 3 is pushed through a thrombus 22, and the cage 3 is located distally of the thrombus and the blocking body 5 is located proximally of within the thrombus.

FIG. 3C: In the third step, the cage 3 and blocking body 5 are deployed on each side of the thrombus segment 22.

FIG. 3D: In the fourth step, the cage 3 is moved proximally towards the blocking body 5 along the longtitudinal axis of the device in the direction of the arrow A, while keeping the blocking body axially stationary, and forcing the thrombus into the cage through the coarse mesh at the distal end 10 of the cage 3. Although not shown, physician specified fluids can be introduced into the space between the cage 3 and blocking body 5 to help soften or disrupt the clot composition before or during the actuation means of the device.

FIG. 3E: In the fifth step, the extractor mechanism is actuated to continuously remove thrombus 22 from the cage 3 as the cage 3 is moved towards the blocking body 5.

The device of the invention also preferably comprises a cone shaped capture device such that the thrombus is forced into a position close to the central axis position of the catheter where the thrombus is macerated and extracted.

The device of the invention also preferably comprises a vibration mechanism that is configured to vibrate the device, the catheter member, or one or both of the capture or blocking body. The vibration mechanism may be employed with devices having one or two radially expansible bodies. The purpose of the vibration mechanism is to cause the catheter or each cage forming part of the device vibrate against the walls of the vessel, which has been shown to improve the removal of thrombus from the walls of blood vessels. FIGS. 8 to 11 show a number of different embodiments of the vibration mechanism, all of which employ a rotatable member that is unbalanced, or eccentric, with respect to a longtitudinal axis of the device. Other methods of vibrating the catheter member or capture body will be apparent to a person skilled in the art In a first embodiment (FIG. 4), the device 1 comprises a cage 3 and a helical member 7 arranged on a rotating shaft 31 extending longitudinally along the device 1. A length 32 of the helical member 30 and shaft 31, disposed within the catheter member 2, is disposed along an axis that is displaced with respect to the longtitudinal axis of the catheter member, resulting in the length of the helical member 30 and shaft 31 rotating eccentrically with respect to the longtitudinal axis of the catheter, and thereby causing vibration of the cage. Vibration of the cage helps dislodge thrombus from the walls of the vessel, and thereby assists in removal of thrombus from the vessel.

In a second embodiment (FIG. 5), in which parts described with reference to the previous embodiment are assigned the same reference numerals, a coil 33 or a number of coils of the helical screw 7 is configured eccentrically with respect to the shaft 31, thereby causing vibration of the helical member and consequently vibration of the device including the catheter or each cage forming part of the device.

FIG. 6 shows a vibration mechanism comprising a cam 35, and is displacement and not weight/force based. Rotation of the cam 35 around the centre point 36 causes the cage to vibrate in a cyclical manner. High speed rotation cause more significant vibration.

In a forth embodiment (FIG. 7), which is similar to the embodiment of FIG. 6, the vibration mechanism comprises an unbalanced weight 37 configured to rotate about a longtitudinal axis of the catheter member. Rotation of the unbalanced weight causes the cage to vibrate during use.

As described above, various means for deploying the cage and blocking body may be employed, for example pneumatic or hydraulic expansion of balloons or the use of control arms attached to each end of the cage or blocking body, where relative movement of the arms causes the cage or blocking body to expand or collapse. In another embodiment, illustrated in FIG. 8, the deployment means comprises a retaining sheath 50 shows an embodiment of the device of the invention in which a sheath 50 is provided that covers the elongated catheter member 2 and keep the cage 3 and blocking body (not shown) in an unexpanded orientation. In this embodiment, the device can be actuated to withdraw the sheath thereby allowing the cage and blocking body expand (deploy) to their expanded configuration. Use of this deployments means requires that the cage and blocking body are self-expanding, for example due to an inherent property of the cage or body, for example elasticity.

Figure 11:
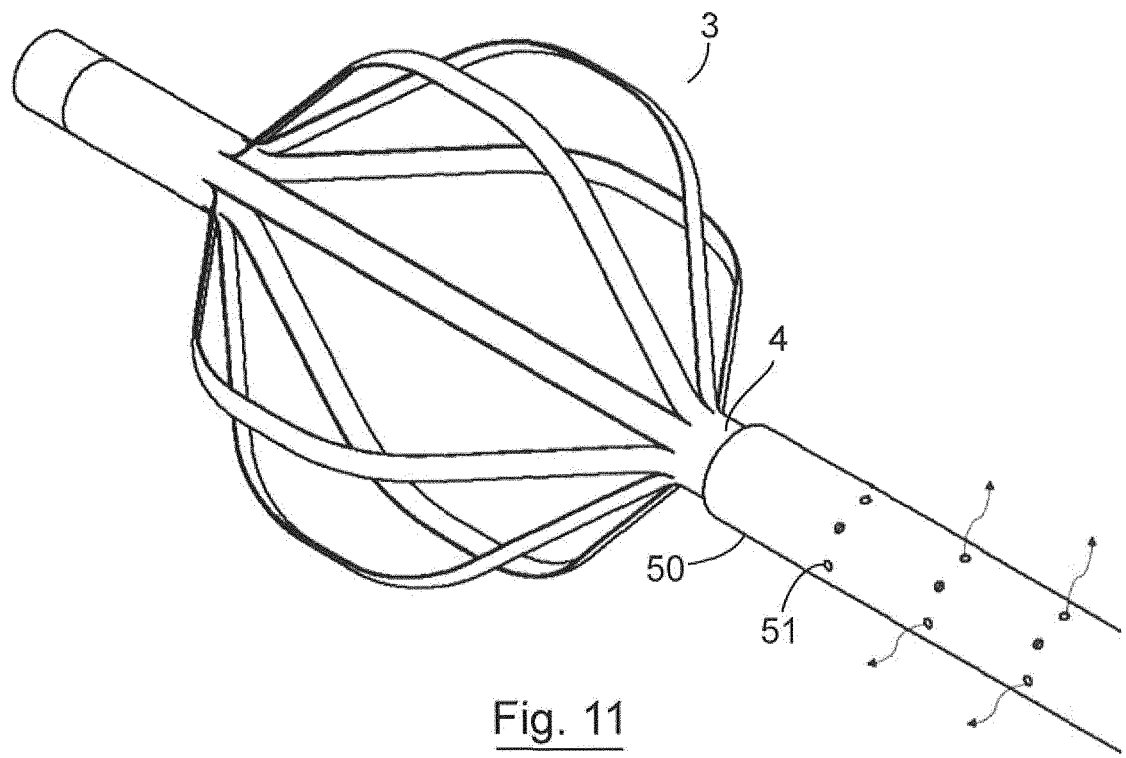

As described above, the device of the invention may also be employed to deliver liquid agent, for example a thrombolytic agent which can break down thrombus, to the vessel lumen. This may be achieved in a number of different ways including:

The direction of rotation of the extractor screw can be changed to infuse rather than extract.
Inject through the hollow distal arm.
Inject through a lumen between the distal control arm and the extractor tube (proximal arm) (FIG. 9)
Injected in between the extractor tube (proximal arm) and the sheath (FIG. 10).
Injected through cavities 51 in the sheath 50 (FIG. 11).
The location of the sheath and cavities can be adjusted along the catheter length.
One of, or a combination of, the above methods of infusion.

Generally, the liquid agent would be injected into the delivery lumen, which may be any of the above. Alternatively, the liquid agent may be delivered slowly by means of a drip feed, or may be delivered in a number of different ways, for example through a hollow distal arm (which has the advantage of being capable of delivering liquid agent distally of the cage), through a lumen formed between the distal arm and the proximal arm (also referred to as the extractor tube), or through a lumen formed between the proximal arm and the outer sheath.

FIG. 12 shows an alternative embodiment of the device (similar to the device of FIG. 1) in which parts identified with reference to the previous embodiments are assigned the same reference numerals. In this device, the blocking body 5 is dimensioned to "dove-tail" or overlap in a radial and axial direction with the inwardly tapering leading end 10 of the cage 3. Thus, when the body 5 and cage 3 are brought together, they can abut closely thus forcing thrombus into the cage 3 for maceration or extraction. The blocking body may deform or be actuated to deform to achieve this overlapping configuration. In this embodiment, a lumen for delivery of thrombolytic agent is provided between the blocking body control arm 6 and the control arm 4 of the cage 3.

FIG. 13 shows an alternative embodiment of the device in which parts identified with reference to the previous embodiments are assigned the same reference numerals. In this embodiment, the blocking body is adapted to deform into a dovetailing shape upon engagement with the capture body 3. Specifically, the blocking body has an axial extension that projects towards the capture body, and engagement between the leading end of the capture body and the projection causes the blocking body to invert from the shape shown in FIG. 13A to the shape shown in FIG. 13B. In use the body and cage may then be brought together into a dovetailing arrangement (as shown in FIG. 13B) or they may be maintained in a spaced-apart, non-overlapping, arrangement.

In another embodiment, the capturing body and the blocking body may operatively connected to elongated catheter member 2 and or control arm 4. Inversion or collapsing of the blocking body or the capturing body causes the distance between the capturing body and the blocking body to be reduced such that they can abut closely thus forcing thrombus into the cage 3 for maceration or extraction. In another embodiment, the inversion or collapsing of the blocking body or the capturing body causing the distance between the capturing body and the blocking body to be reduced such that the thrombus is engaged or trapped between the blocking body and capturing body for subsequent extraction from the body.

The invention is not limited to the embodiments hereinbefore described which may be varied in construction and detail without departing from the spirit of the invention.

The invention claimed is:

1. A thrombectomy device for removing matter from a body lumen, the device comprising:
   a catheter member having a proximal part and a distal part;
   a thrombus blocking body disposed adjacent the distal part of the catheter member and radially expandable between a contracted orientation and an expanded, thrombus-blocking orientation configured to stop proximal movement of thrombi, the thrombectomy device including only one thrombus blocking body;
   a thrombus capture cage disposed at a distal-most end of the catheter member, in an axially spaced-apart relationship to the thrombus blocking body, and positioned distally of the thrombus blocking body, the thrombus capture cage being radially expandable between a contracted orientation and an expanded, thrombus-capture orientation;
   a control arm operably connected to the thrombus capture cage and configured to move the thrombus capture cage axially along the body lumen, wherein the control arm is operably connected to a proximal end of the thrombus capture cage; and an extractor, the extractor having an extractor tube and an auger, the extractor tube including a distal open end disposed within the thrombus capture cage, and the auger extending through the extractor tube and distal of the distal open end of the extractor tube, wherein the thrombus blocking body includes an axial extension that projects towards the thrombus capture cage, the axial extension including an outer periphery of the thrombus blocking body.

2. The device according to claim 1, wherein at least one of the thrombus capture cage and the thrombus blocking body is self-expanding.

3. The device according to claim 2, wherein the control arm is a first control arm, and the device further includes a second control arm operably connected to a distal end of the thrombus capture cage.

4. The device according to claim 3, further including a spring biasing the thrombus capture cage toward the expanded orientation.

5. The device according to claim 3, wherein the thrombus capture cage includes a mesh, the mesh being a finer mesh at the distal end of the thrombus capture cage than at the proximal end of the thrombus capture cage.

6. The device according to claim 5, wherein the thrombus capture cage includes a scraping edge extending circumferentially around the thrombus capture cage at a widest point of the thrombus capture cage.

7. The device according to claim 6, wherein the thrombus capture cage is rotatable with respect to the catheter member and the thrombus blocking body.

8. The device according to claim 6, wherein the auger extends distal of the scraping edge.

9. The device according to claim 3, further including a third control arm operably connected to the thrombus blocking body for moving the thrombus blocking body.

10. The device according to claim 1, further including suction operably connected through the extractor tube to the distal open end.

11. The device according to claim 1, further including a macerator located within the thrombus capture cage and disposed closer to the distal end of the thrombus capture cage than the extractor.

12. The device according to claim 1, further including a restraining sheath movable to cover or uncover the thrombus blocking body and the thrombus capture cage.

13. The device according to claim 1, further including liquid delivery to a location distal of the thrombus blocking body.

14. A thrombectomy device for removing matter from a body lumen, the device comprising:
a catheter member having a proximal part and a distal part;
a thrombus blocking body disposed adjacent the distal part of the catheter member and radially expandable between a contracted orientation and an expanded, thrombus-blocking orientation configured to exert force against a wall of the body lumen and stop proximal movement of thrombi, the thrombectomy device including only one thrombus blocking body;
a thrombus capture cage disposed at a distal-most end of the catheter member, in an axially spaced-apart relationship to the thrombus blocking body, and positioned distally of the thrombus blocking body, the thrombus capture cage being radially expandable between a contracted orientation and an expanded, thrombus-capture orientation configured to exert force against a wall of the body lumen;
a control arm operably connected to the thrombus capture cage and configured to move the thrombus capture cage axially along the body lumen, wherein the control arm is operably connected to a proximal end of the thrombus capture cage; and
an extractor, the extractor having an extractor tube and an auger, the extractor tube including a distal open end disposed within the thrombus capture cage, and the auger extending through the extractor tube and distal of the distal open end of the extractor tube,
wherein the thrombus blocking body includes a dovetail shape including an axial extension that projects towards the thrombus capture cage, and engagement between the thrombus capture cage and the extension causes the thrombus blocking body to surround a proximally tapering portion of the thrombus capture cage.

15. The device according to claim 14, further including suction operably connected through the extractor tube to the distal open end.

16. The device according to claim 15, further including a thrombus macerator having one or more rotating elements configured to contact the thrombus located within the cage and dislodge the thrombus or break-up the thrombus into smaller particles.

17. The thrombectomy device of claim 14, where the axial extension includes an outer periphery of the thrombus blocking body.

18. A thrombectomy device for removing matter from a body lumen, the device comprising:
a catheter member having a proximal part and a distal part;
a thrombus blocking body disposed adjacent the distal part of the catheter member and radially expandable between a contracted orientation and an expanded, thrombus-blocking orientation, the thrombectomy device including only one thrombus blocking body;
a thrombus capture cage disposed at a distal-most end of the catheter member, in an axially spaced-apart relationship to the thrombus blocking body, and positioned distally of the thrombus blocking body, the thrombus capture cage being radially expandable between a contracted orientation and an expanded, thrombus-capture orientation;
a control arm operably connected to the thrombus capture cage and configured to move the thrombus capture cage axially along the body lumen, wherein the control arm is operably connected to a proximal end of the thrombus capture cage; and
an extractor, the extractor having an extractor tube and an auger, the extractor tube including a distal open end disposed within the thrombus capture cage, and the auger extending through the extractor tube and distal of the distal open end of the extractor tube,
wherein the thrombus blocking body in the expanded, thrombus-blocking orientation, and the thrombus capture cage in the expanded, thrombus capture orientation, in the axially spaced-apart relationship, are configured to form a thrombus-trapping space together with a wall of the body lumen,
wherein the thrombus capture cage includes a proximally tapering portion, and
wherein the thrombus blocking body includes a dovetail shape, and engagement between the thrombus capture cage and the thrombus blocking body causes the thrombus blocking body to surround the proximally tapering portion of the thrombus capture cage.

* * * * *